United States Patent
Grass et al.

(10) Patent No.: US 7,020,317 B2
(45) Date of Patent: Mar. 28, 2006

(54) COMPUTED TOMOGRAPHY APPARATUS

(75) Inventors: Michael Grass, Hamburg (DE);
Thomas Koehler, Norderstedt (DE);
Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 742 days.

(21) Appl. No.: 10/135,265

(22) Filed: Apr. 30, 2002

(65) Prior Publication Data
US 2002/0186871 A1    Dec. 12, 2002

(30) Foreign Application Priority Data
May 2, 2001    (DE) ................. 101 21 441

(51) Int. Cl.
*G06K 9/00*    (2006.01)

(52) U.S. Cl. ................. 382/131; 250/492.1; 378/4; 378/15; 378/901

(58) Field of Classification Search ............ 382/128, 382/131; 73/23.1; 250/338.5, 363.02, 363.03, 250/363.04, 492.1; 378/4, 15, 19

See application file for complete search history.

(56) References Cited

U.S. PATENT DOCUMENTS

| | | | |
|---|---|---|---|
| 5,974,110 A | | 10/1999 | Hu |
| 6,240,157 B1 * | | 5/2001 | Danielsson ............. 378/15 |
| 6,269,141 B1 * | | 7/2001 | Proksa et al. ........... 378/19 |
| 6,327,331 B1 * | | 12/2001 | Toth et al. ............. 378/20 |

FOREIGN PATENT DOCUMENTS

| | | |
|---|---|---|
| EP | 0 969 414 | 1/2000 |
| WO | WO 99/36885 | 7/1999 |

OTHER PUBLICATIONS

Besson, Guy; New Classes of Helical Weighting Algorithms with Applications to Fast CT Reconstruction; Medical Physics, American Institute of Physics; vol. 25, No. 8, Aug., 1998, pp. 1521-1532.

* cited by examiner

*Primary Examiner*—Sheela Chawan
(74) *Attorney, Agent, or Firm*—Thomas M. Lundin

(57) ABSTRACT

The invention relates to a computed tomography apparatus in which the measuring data acquired in a first measuring window enter the reconstruction with a weight other than that of the measuring data that can be acquired in a second measuring window, the second measuring window being situated centrally relative to the first measuring window and being smaller than the first measuring window. Depending on the weighting of the measuring data, the resultant CT image exhibits either smaller motional artefacts or a spatially more uniform noise.

5 Claims, 4 Drawing Sheets

COMPUTED TOMOGRAPHY APPARATUS

BACKGROUND

The invention relates to a computed tomography apparatus which includes a radiation source which emits a conical radiation beam, which apparatus involves a helical relative motion between the radiation source and the examination zone. The invention also relates to a computer program for such a computed tomography apparatus.

A computed tomography apparatus of this kind is known already from WO 9936885 (PHQ 98020). The helix and the detector unit which detects the conical radiation beam to the other side of an examination zone are proportioned in such a manner that the detector unit detects all rays of the radiation beam which extend through two neighboring segments of the helix which face the radiation source or extend between these segments. The reconstruction utilizes only the measuring data from the detector unit which is associated with the rays in the measuring window thus defined.

Upon its entry into the conical radiation beam, an arbitrary point in the examination zone is irradiated from a direction which is 180° opposed to the direction wherefrom it is irradiated upon its departure from the radiation beam. Because each point in the examination zone is irradiated only through an angular range of exactly 180°, this method is very susceptible to scanning errors.

This susceptibility is reduced in a computed tomography apparatus which is known from U.S. application Ser. No. 09/368,850 (PHD 98086); the computed tomography apparatus disclosed therein is distinct from the previously mentioned known computed tomography apparatus in that the measuring data used for the reconstruction is situated within a measuring window which is a factor of 2n+1 larger in relation to the distance between two neighboring turns of the helix, n being an integer number amounting to at least 1. According to this method each point of the examination zone is irradiated from an angular range of (2n+1). 180°. The susceptibility to scanning errors is then less pronounced. This advantage is achieved at the expense of the fact that the object to be examined is irradiated by a factor of 2n+1 longer (with the same speed of rotation). In the case of a moving object, this fact may give rise to motional unsharpness. Moreover, it may give rise to specific artefacts in the reconstructed CT image.

SUMMARY

It is an object of the present invention to provide a computed tomography apparatus in which the described problems are mitigated. This object is achieved in accordance with the invention by means of a computed tomography apparatus which includes a scanning unit which includes a radiation source and a detector unit which is connected thereto in order to detect a conical radiation beam, emitted by the radiation source, after its passage through an examination zone or an object present therein, a drive device for producing a relative motion in the form of a helix, consisting of a rotation about an axis of rotation and an advance in the direction parallel to the axis of rotation, between the scanning unit and the examination zone or the object, the helix and the detector unit being proportioned in such a manner that the detector unit simultaneously detects all rays of the radiation beam within a first measuring window whose edges, being offset relative to one another in the direction of the axis of rotation, are defined by lines which originate from the radiation source and intersect two segments of the helix which are offset over the distance $(2n+1)p$ in the direction of the axis of rotation, where n is an integer number $\geq 1$ and p corresponds to the axial offset of two neighboring turns of the helix, and a reconstruction unit for reconstructing a CT image which corresponds to the spatial distribution of the absorption within the examination zone from the measuring data acquired by the detector unit within the first measuring window, the measuring data derived from rays which extend within a second measuring window being assigned a weight for the reconstruction which differs from that assigned to the measuring data from rays which extend outside the second measuring window but inside the first measuring window, and the second measuring window being situated, viewed in the direction of the axis of rotation, at the center of the first measuring window and its mutually offset edges being defined by lines which originate from the radiation source and intersect two segments of the helix which are offset over the distance $(2m+1)p$ in the direction of the axis of rotation, where m is an integer number and $0 \leq m \leq n$.

Thus, like in the latter known computed tomography apparatus, in accordance with the invention measuring data is acquired from rays which are situated within a (first) measuring window which (measured in the direction of the axis of rotation) is a factor of 2n+1 larger than the distance between two neighboring turns of the helix. During the reconstruction, however, measuring data from a second, smaller measuring window which is centrally situated with respect to the first measuring window is assigned a weighting factor which differs from that assigned to the measuring data acquired outside the second measuring window but within the first measuring window.

The invention is based on the idea that the examination zone can be completely reconstructed from the measuring data acquired in the first measuring window as well as from the measuring data acquired in the second measuring window. When the CT images formed by such different reconstruction are added, the described problems are more or less suppressed. A reduced susceptibility to scanning errors is achieved (in comparison with a computed tomography apparatus with a measuring window between two neighboring turns) and the motional unsharpness and any other artefacts are reduced (in comparison with a computed tomography apparatus with a measuring window which extends across several turns of the helix). Because of the linearity of the reconstruction method, the processing of the measuring data is equivalent, depending on whether this data was acquired in the second measuring window or only in the first measuring window, to the weighted summing of the two CT images separately reconstructed from the CT data of the first and the second measuring window, respectively.

The principle on which the invention is based can also be extended to more than two measuring windows as indicated in claim 2. A prerequisite in this respect is that the first measuring window must extend across a range of at least 5p in the axial direction ($n \geq 2$) and that the further window is smaller than the first window and larger than or smaller than the second window.

The possibility for selection of the weights with which the measuring data derived from the various measuring win dows enter the reconstruction as disclosed in claim 3 enables the weights to be adapted to different conditions in the examination zone. If there is a high risk of motional unsharpness, it makes sense to attach more weight to the measuring data acquired in the second measuring window. Otherwise it is effective to put less emphasis on this measuring data.

The measuring data from the two windows can in principle be processed in an identical way, that is, if their different weight is ignored. However, in conformity with claim 4 it is also possible to process the measuring data in different ways. This is because, when the second measuring data is bounded by neighboring turns of the helix (m=0), the filtering of the measuring data from this window can be carried out as described in U.S. application Ser. No. 09/663,634 (PHD 99123), thus resulting in an enhanced image quality.

Claim 5 describes a computer program for the reconstruction unit of a computed tomography apparatus which enables implementation of the invention in a computed tomography apparatus.

DRAWINGS

The invention will be described in detail hereinafter with reference to the drawing. Therein:

DESCRIPTION

Figure 1:
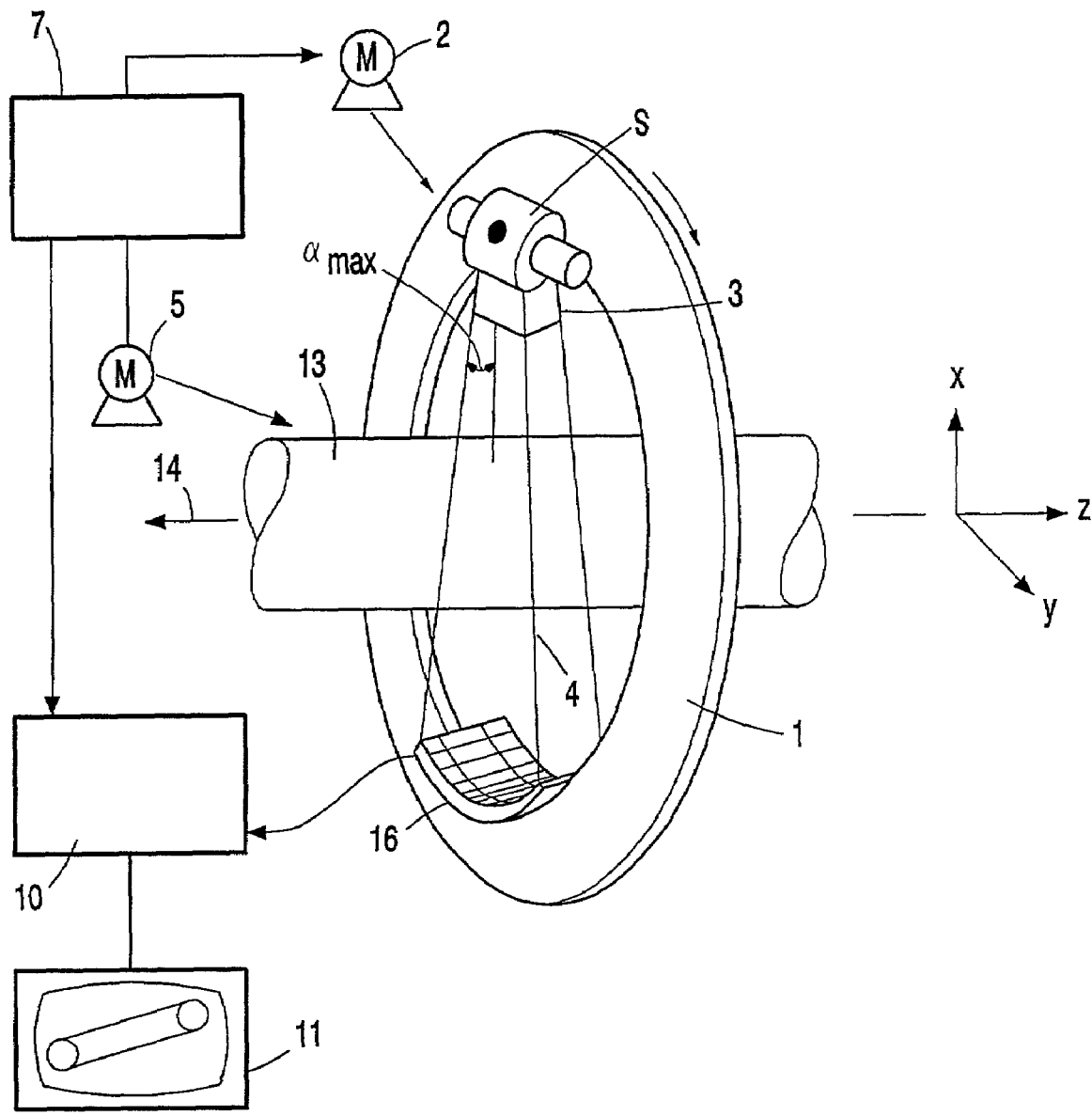
FIG. 1 shows a computed tomography apparatus in accordance with the invention.

The computed tomography apparatus as shown in FIG. 1 includes a gantry 1 which is capable of rotation about an axis of rotation 14 which extends parallel to the z direction of the co-ordinate system shown in FIG. 1. To this end, the gantry is driven at a preferably constant angular speed by a motor 2. A radiation source S, for example, an X-ray tube, is mounted on the gantry. The X-ray source is provided with a collimator device 3 which forms a conical radiation beam 4 from the radiation produced by the radiation source S, that is, a radiation beam which has a finite dimension other than zero in the direction of the z axis as well as in a direction perpendicular thereto (that is, in the x-y plane).

The radiation beam 4 traverses an object (not shown) which is present in an examination zone 13. The examination zone 13 is shaped as a cylinder. After having traversed the examination zone 13, the X-ray beam 4 is incident on a detector unit 16 which is mounted on the gantry 1 and includes a number of detector rows which are offset in the z direction. Each detector row is arranged in a plane which extends perpendicularly to the z direction and comprises a plurality of detector elements, each of which detects a respective ray and delivers corresponding measuring data. The detector unit 16 may be arranged on an arc of circle around the axis of rotation 14, but other detector geometries are also feasible; for example, it may be arranged on an arc of circle around the radiation source S.

The angle of aperture $\alpha_{max}$ of the radiation beam 4 (the angle of aperture is defined as the angle enclosed by a ray of the beam 4 which is situated at the edge in the x-y plane relative to the plane defined by the radiation source S and the axis of rotation 14) then determines the diameter of the examination zone. The examination zone 13, or an object present therein, for example, a patient accommodated on a patient table, can be displaced parallel to the z axis. The speed of such displacement in the z direction is constant and preferably adjustable.

The measuring data acquired by the detector unit 16 is applied to an image processing computer 10 which reconstructs therefrom the absorption distribution in the part of the examination zone 13 which is irradiated by the radiation cone 4 in order to reproduce it, for example on a monitor 11. The two motors 2 and 5, the image processing computer 10, the radiation source S and the transfer of the measuring data from the detector unit 16 to the image processing computer 10 are controlled by a suitable control unit 7.

When the motor 5 stands still and the motor 2 rotates the gantry, a circular scanning motion of the radiation source S and the detector unit occurs. The control unit 7, however, can also activate the motors 2 and 5 simultaneously, that is, in such a manner that the ratio of the speed of advancement of the examination zone 13 to the angular velocity of the gantry is constant. In this case the radiation source S and the examination zone 13 move relative to one another along a helical trajectory.

Figure 2:
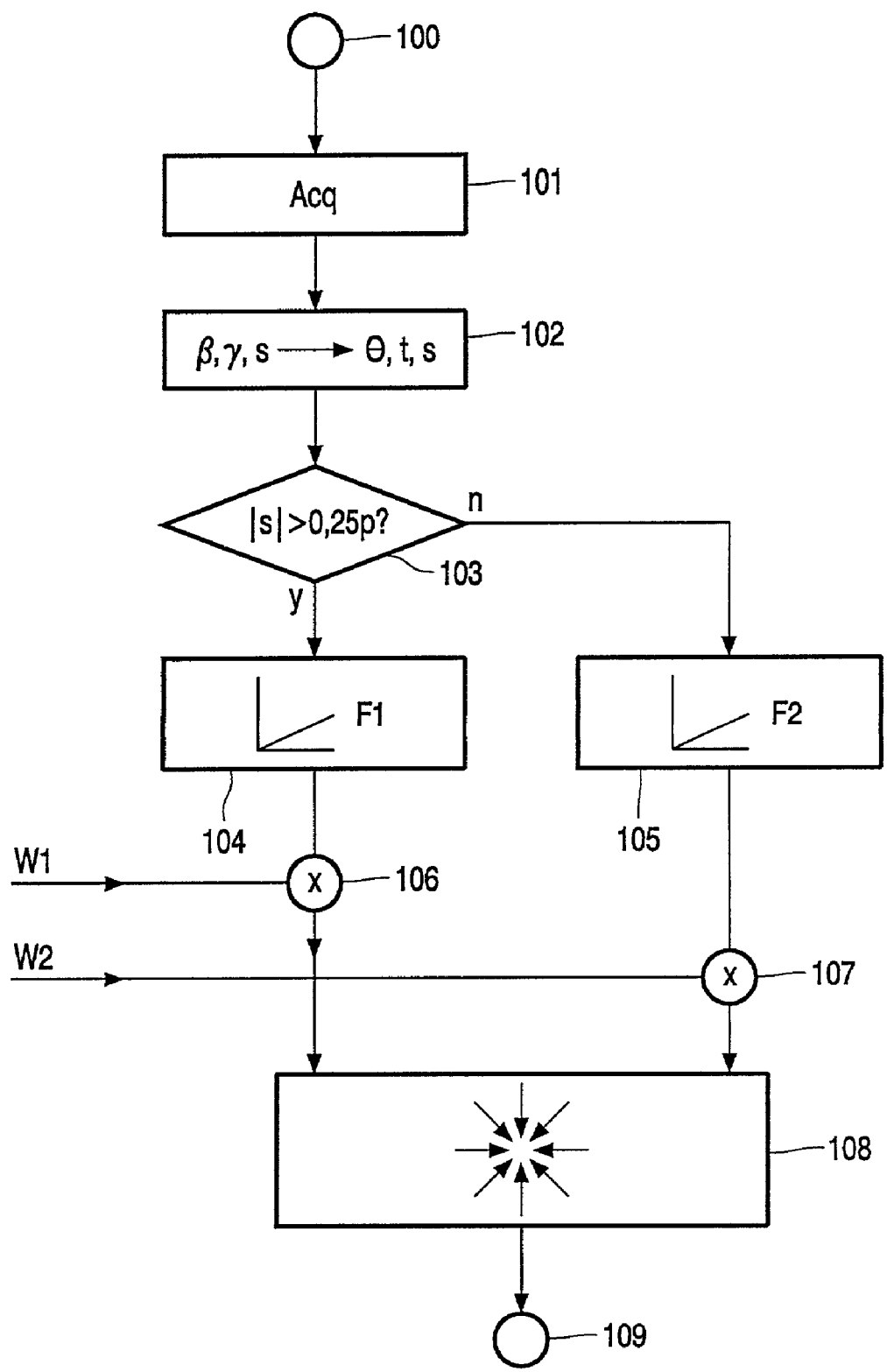
FIG. 2 shows a flowchart of the method carried out by means of such a computed tomography apparatus.

The acquisition of measuring data by means of the computed tomography apparatus as shown in FIG. 1 and the reconstruction of a CT image from such measuring data will be described in detail hereinafter with reference to the flowchart which is shown in FIG. 2.

After the initialization in the step 100, the motors 2 and 5 are activated and the radiation source S is switched on. The measuring data subsequently acquired in the step 101, being dependent on the attenuation of the radiation beam in the examination zone, is transferred from the detector unit 16 to a memory of the reconstruction unit 10.

Figure 3:
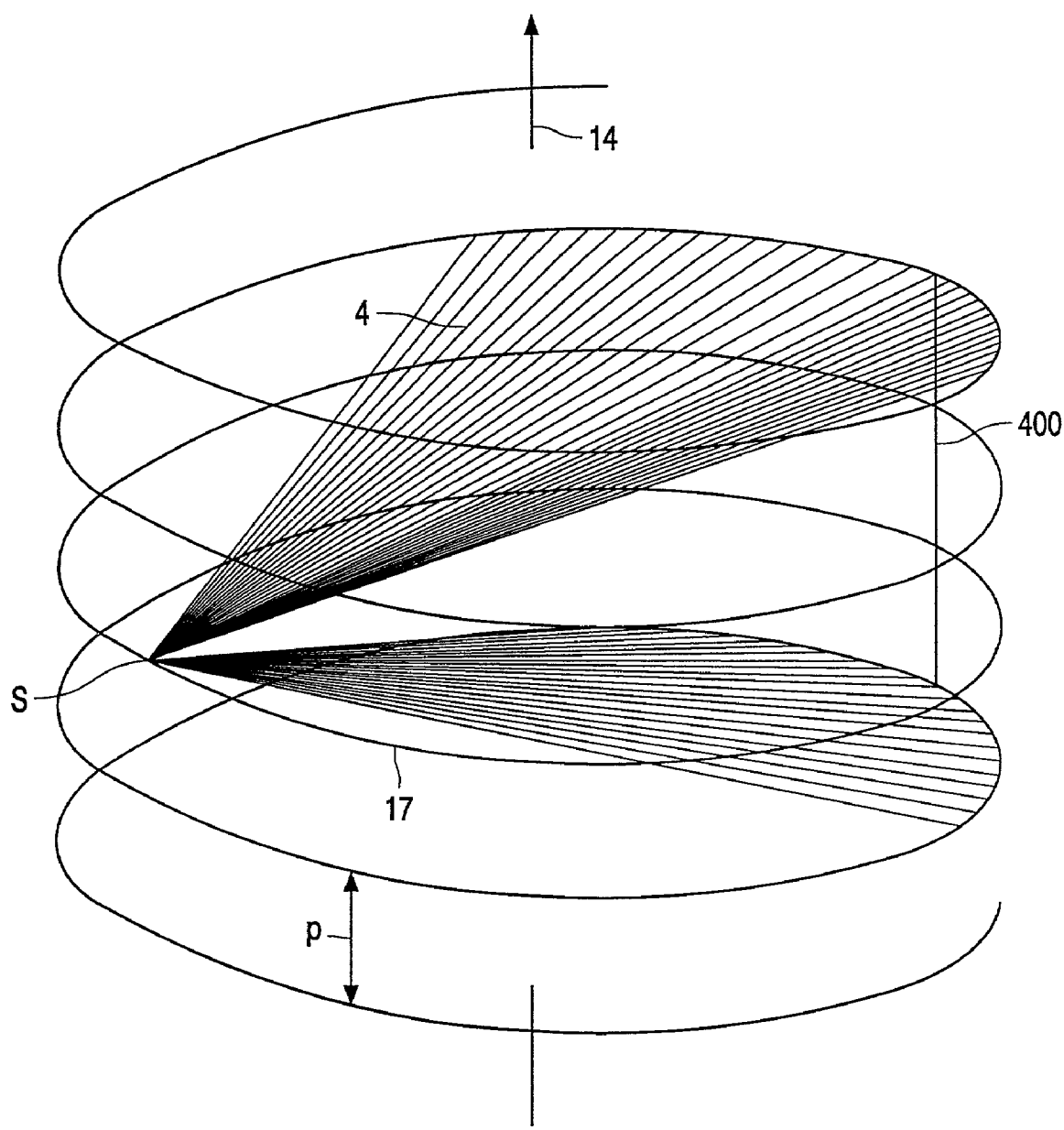
FIG. 3 shows the location in space of the radiation source and the edge rays of the measuring window relative to the helix.

FIG. 3 shows the geometrical conditions during the acquisition of the measuring data. In this respect it is assumed that the radiation source S moves along a trajectory 17 in the form of a helix around the stationary examination zone which is not shown in FIG. 3, even though it actually performs only a circular motion and the examination zone or the object to be examined is displaced. However, this assumption is permissible because only the relative motion between the X-ray source and the examination zone is of relevance.

The radiation beam 4 used for the reconstruction is limited to a first measuring window. The lines or edge rays of the radiation beam 4 which are shown in the drawing and originate from the radiation source intersect the edges of said measuring window which are mutually offset in the direction of the axis of rotation and also intersect two of the turns of the helix which face the radiation source. Thus, only rays which coincide with the edge rays shown or are situated between these edge rays are evaluated for the measurement. The measuring window is situated symmetrically relative to the radiation source S. The turns of the helix which define the edge of the measuring window are situated at a distance 3p from one another in the direction of the axis of rotation, where p is the distance between two neighboring turns of the helix.

Figure 4:
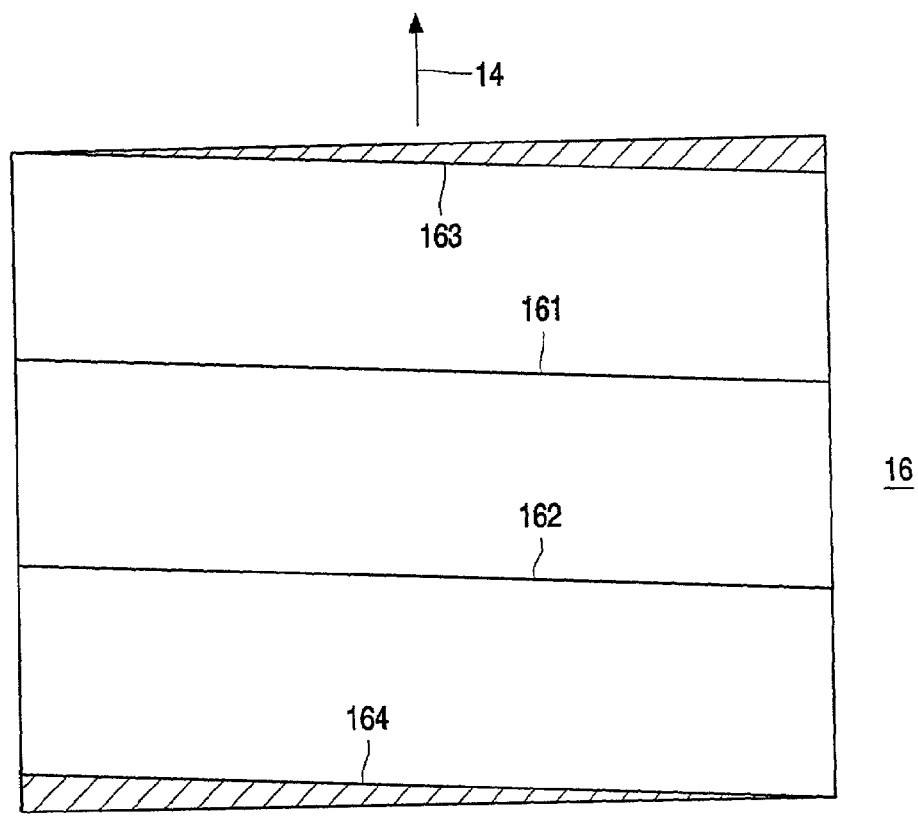
FIG. 4 shows a development of the detector unit.

FIG. 4 shows a development of the detector unit 16; for the sake of clarity, the dimensions of the detector unit are shown at a significantly enlarged scale in the direction of the axis of rotation in comparison with its dimensions in the direction perpendicular thereto. The reference numerals 163 and 164 denote the edges of the first measuring window on the detector unit which are mutually offset in the direction of the axis of rotation. Because of the slope of the helix, said edges do not extend horizontally but are inclined. If the detector 16 were curved around the radiation source S instead of around the axis of rotation 14, or if it were flat, the edges 163 and 164 would not be straight as shown in FIG. 4.

FIG. 4 also shows a second measuring window whose edges which are offset in the direction of the axis of rotation 14 are denoted by the reference numerals 161 and 162. The edges are defined by the lines which originate from the radiation source S and puncture the two turns inside the first measuring field and these edges at the same time.

An arbitrary point in the examination zone is projected onto a detector element upon its entry into the first measuring window, which detector element is situated, for example, on the lower edge 164 (in that case the ray on which the point is situated punctures a turn of the helix). Subsequently, this point is projected onto a detector element on the line 162 (in that case the ray through the point punctures a neighboring turn) which bounds the second measuring window in the downward direction. After having traversed a further radiation range of 180°, this point is projected onto a detector element on the upper edge 161 of the second measuring window (where the ray punctures the next turn). When this point has been irradiated through an angular range amounting to 540° overall by the radiation source S, it is projected onto a detector element which is situated on the upper edge 163 of the first measuring window (the ray then intersects the upper turn).

The path of the radiation beam 4 which is compatible with the first measuring window can be realized by appropriate configuration of the collimator 3. If this is not possible so that the radiation beam 4 irradiates the entire rectangular zone of the detector 6, the limitation to the measuring window is realized by excluding the measuring data from detector elements which are situated in the shaded zones outside the lines 163 and 164 from the reconstruction.

The measuring data acquired in the step 101 correspond (that is, possibly after smoothing and logarithmation) to the line integral of the attenuation along the ray along which it has been measured. If necessary, in this step all measuring data can be weighted with the cosine of the angle which is enclosed by the relevant ray relative to a plane perpendicular to the axis of rotation. However, when the cosine has practically the value 1 for all rays (because the angle is very small), such weighting can be dispensed with.

All measuring data M is characterized by a (scalar) quantity which corresponds to the line integral of the attenuation and by the position of the rays along which it has been acquired. Each ray is characterized by the three parameters ($\beta$, $\gamma$, s) listed below.

The parameter $\beta$ characterizes the direction of a normal from the radiation source position to the axis of rotation 14 in an (x,y) plane which extends perpendicularly to the axis of rotation. All rays in the radiation beam shown in FIG. 3 thus have the same parameter $\beta$. After more than one revolution of the radiation source, $\beta$ will be larger than $2\pi$.

The parameter $\gamma$ is the angle enclosed by the relevant ray in the (x,y) plane, perpendicular to the axis of rotation 14, relative to the said normal. All rays within a fan beam parallel to the axis of rotation have the same value $\gamma$. In FIG. 3 such a fan beam is defined by the line 400 and the (edge) rays which connect said line to the radiation source (S).

The parameter s represents the height co-ordinate of the ray, that is, it indicates the position in which the relevant ray passes between two turns of the helix. All rays which intersect the same turn of the helix have the same value s. The edge rays of the first measuring window are characterized by the parameter s=±0.75 p; the edge rays of the second measuring window have the parameter s=±0.25 p.

Each ray is thus characterized by a point in the three-dimensional ($\beta$, $\gamma$, s) parameter space. The acquisition of the CT data thus constitutes a sampling of the so-called object function (in this case of the line integral of the attenuation) in a multitude of sampling points which are comparatively uniformly distributed in the ($\beta$, $\gamma$, s) parameter space. The sampling in this parameter space, however, is not optimally suitable for the further processing.

Therefore, in the step 102 a so-called rebinning operation is performed in a parallel beam geometry. Therein, a data set M($\theta$, t, s) which represents the object function at the grid points of a regular Cartesian grid in a three-dimensional ($\theta$, t, s) parameter space is calculated by resorting and re-interpolation from the acquired measuring data M($\beta$, $\gamma$, s):

The parameter $\theta$ therein indicates the direction of a fan beam which is parallel to the axis of rotation in a plane perpendicular to the axis of rotation. The rays in fan beams which extend parallel to the axis of rotation and to one another have the same parameter $\theta$. Like the parameter $\beta$, the parameter $\theta$ may also become larger than $2\pi$.

The parameter t denotes the distance between a fan beam and the axis of rotation; the fan beams which are situated to one side of the axis of rotation then have a negative value of t whereas the fan beams situated to the other side have a positive value of t. The maximum value of t corresponds to the radius of the examination zone 13.

The parameter s once more is the height co-ordinate.

Except for the use of a second measuring window, the method described thus far is known from the cited U.S. application Ser. No. 09/368,850. However, whereas in conformity with the known method the further processing of the measuring data takes place independently of its position within the (first) measuring window, the measuring data in accordance with the invention is further processed in dependence on whether or not it is associated with rays which also extend through the second measuring window.

Therefore, in the step 103 it is checked whether the absolute value s of the measuring data M($\theta$, t, s) is larger than 0.25 p (where p corresponds to the distance between neighboring turns of the helix). If so, the rays associated with this measuring data extend within the first measuring window, but outside the second measuring window. In this case in the step 104 a one-dimensional filtering operation is applied to all CT data which have the same value of $\theta$ and s but different values of t.

Figure 5:
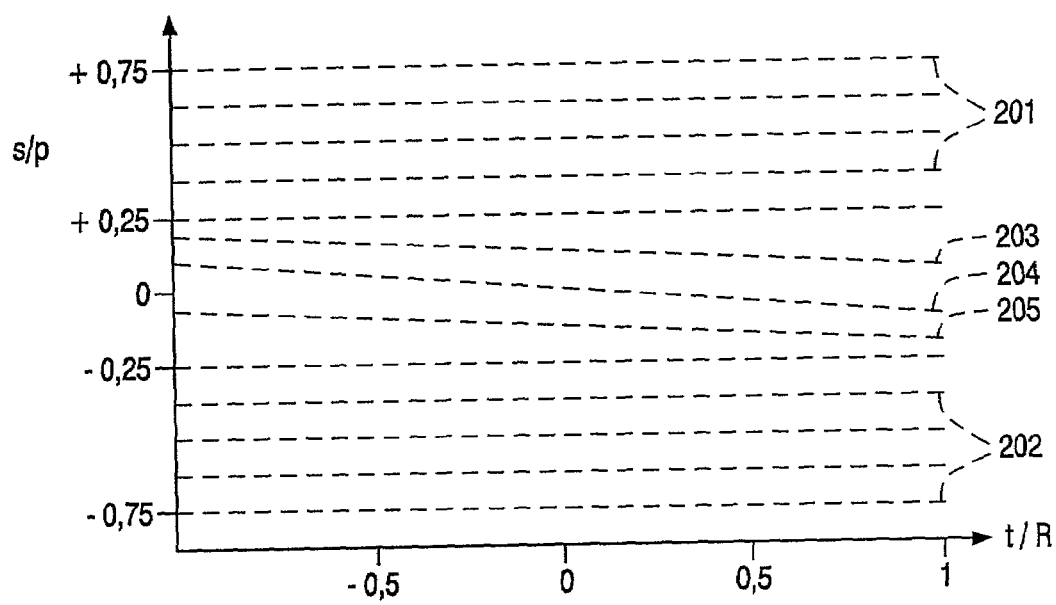
FIG. 5 shows the course of the lines along which a one-dimensional filtering is performed during the reconstruction.

This filtering operation is illustrated in FIG. 5. FIG. 5 shows a plane parallel to the $\theta$ axis in the cartesian ($\theta$, t, s) parameter space; the parameter s is the ordinate (normalized to the value p) and the parameter t (normalized to the radius R of the examination zone) is the abscissa. The dotted and dot-dash lines connect the successive grid points or measuring data subjected to a common filtering operation. Such lines extend horizontally for all measuring data for which the value s is between 0.25p and 0.75p as well as for those where it lies between -0.75p and -0.25p, for example, the lines 201 and 202.

All measuring data situated within the second measuring window (that is, measuring data whose parameter s is not larger than 0.25p and not smaller than -0.25p) are subjected to a filtering operation in the block 105; however, the measuring data which are situated on a horizontal line are not subjected to one-dimensional filtering, but only the measuring data of rays which are interconnected by more or less inclined lines 203, 204 and 205 in FIG. 5. This filtering method is described in detail in U.S. application Ser. No. 09/663,634 whereto explicit reference is made. This filtering operation results in a given improvement of the image quality.

The measuring data acquired outside the second measuring window (but inside the first measuring window) is weighted with a weighting factor $w_1$ (block 106) and the measuring data acquired within the second measuring window and filtered in the step 105 is weighted with a second weighting factor $w_2$ (block 107). In the step 108 the attenuation in the individual points of the examination zone is derived by backprojection from the measuring data thus filtered and weighted. For each point in the examination zone the rays are then determined which have irradiated this point of the examination zone from an angular range of $3\pi$. The measuring data associated with these rays is weighted with $w_1$ or $w_2$ so as to be summed, that is, after a further interpolation, if necessary. The image thus reconstructed is reproduced and stored in a suitable manner. The method is thus terminated (block 109).

The weighting factors $w_1$ and $w_2$ can be iteratively preset by the user. However, they can also be automatically preset as a function of the part of the body to be imaged.

When the weighting factor $w_1=0$ (or small in comparison with $w_2$), only measuring data from the second measuring window will be used for the reconstruction. This results in a CT image which has a low level of motional unsharpness, but an increased susceptibility to scanning errors. When the weighting factor $w_2$ is chosen to be twice as large as the weighting factor $w_1$, the linearity of the reconstruction method ensures that the same conditions will be obtained as when a first CT image were reconstructed from all measuring data acquired in the first window and this CT image were added to a second CT image which is reconstructed exclusively from the measuring data acquired in the second measuring window. The signal-to-noise ratio is then better and the effect of scanning errors is reduced; however, this advantage is achieved at the expense of the fact that any motional unsharpness becomes more pronounced.

When the weighting factors $w_1$ and $w_2$ are equal, essentially the same conditions will be obtained as when a uniformly weighted CT image were reconstructed from all measuring data acquired in the first measuring window. The signal-to-noise ratio is then optimum, but the risk of motional unsharpness is even higher.

Contrary to what is shown in FIG. 2, the measuring data from the second measuring window can also be filtered in the same way as the measuring data from the first measuring window, that is, along parallel lines in the t, s plane (FIG. 5). The branching operation 103 must then be performed only after the uniform filtering. Small reductions of the image quality, however, will have to be accepted in that case.

It has been assumed in the foregoing that the dimensions of the first measuring window in the direction of the axis of rotation correspond to three times the distance p of the turns of the helix. The dimensions of the measuring window, however, may also amount to 3p, 5p or in general to (2n+1)p, where n is an integer number. In that case at least two further measuring windows of the dimensions (2m+1)p and (2k+1)p can be defined (and possibly even more measuring windows), m and k then being different positive integer numbers which are smaller than n. The measuring data from such different measuring windows can be assigned different weighting factors for the reconstruction.

As has already been explained, the same results are obtained when a CT image is reconstructed from all measuring data acquired in a respective measuring window and when this CT image is added to the CT image or the CT images which can be reconstructed from the measuring data of the other measuring window or measuring windows.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A computed tomography apparatus comprising:
    a scanning unit which includes a radiation source (S) and a detector unit (16) which is connected thereto in order to detect a conical radiation beam, emitted by the radiation source, after its passage through an examination zone (13) or an object present therein;
    a drive device (2, 5) for producing a relative motion in the form of a helix (17), consisting of a rotation about an axis of rotation (14) and an advance in the direction parallel to the axis of rotation, between the scanning unit (S, 16) and the examination zone (13) or the object, the helix and the detector unit being proportioned in such a manner that the detector unit simultaneously detects all rays of the radiation beam within a first measuring window whose edges (163, 164), being offset relative to one another in the direction of the axis of rotation (14), are defined by lines which originate from the radiation source (S) and intersect two segments of the helix (17) which are offset over the distance (2n+1)p in the direction of the axis of rotation, where n is an integer number $\geq 1$ and p corresponds to the axial offset of two neighboring turns of the helix; and
    a reconstruction unit (10) for reconstructing a CT image which corresponds to the spatial distribution of the absorption within the examination zone (13) from the measuring data acquired by the detector unit (16) within the first measuring window (160), the measuring data derived from rays which extend within a second window being assigned a weight for the reconstruction which differs from that assigned to the measuring data derived from rays which extend outside the second measuring window but inside the first measuring window, and the second window being situated, viewed in the direction of the axis of rotation, at the center of the first measuring window and its mutually offset edges (163, 164) being defined by lines which originate from the radiation source (S) and intersect two segments of the helix (17) which are offset over the distance (2m+1)p in the direction of the axis of rotation, where m is an integer number and $0 \leq m \leq n$.

2. A computed tomography apparatus as claimed in claim 1, wherein the measuring data derived from rays which extend within at least one additional measuring window enter the reconstruction with a weight which differs from that of the measuring data from rays which extend outside the second measuring window but within the first measuring window, and wherein, viewed in the direction of the axis of rotation, the additional measuring window is situated at the center of the first measuring window and its mutually offset edges (163, 164) are defined by lines which originate from the radiation source (S) and intersect two segments of the helix (17) which are offset over the distance (2k+1)p in the direction of the axis of rotation, where k is an integer number and $0 \leq k \leq n$ and $k \neq m$.

3. A computed tomography apparatus as claimed in claim 1, wherein the weights which are assigned to the measuring data derived from rays from different measuring windows are selectable.

4. A computed tomography apparatus as claimed in claim 1, wherein m=0 and the reconstruction includes one-dimensional filtering of the measuring data as well as backprojection of the filtered data, the filtering of the measuring data associated with the first measuring window being different from the filtering of the measuring data associated with the second measuring window.

5. A computer program embodied in a computer readable medium for the reconstruction unit of a computed tomography apparatus comprising:
   a scanning unit which includes a radiation source (S) and a detector unit (16) which is connected thereto in order to detect a conical radiation beam, emitted by the radiation source, after its passage through an examination zone (13) or an object present therein;
   a drive device (2, 5) for producing a relative motion in the form of a helix (17), consisting of a rotation about an axis of rotation (14) and an advance in the direction parallel to the axis of rotation, between the scanning unit (S, 16) and the examination zone (13) or the object, the helix and the detector unit being proportioned in such a manner that the detector unit simultaneously detects all rays of the radiation beam within a first measuring window whose edges (163, 164), being offset relative to one another in the direction of the axis of rotation (14), are defined by lines which originate from the radiation source (S) and intersect two segments of the helix (17) which are offset over the distance (2n+1)p in the direction of the axis of rotation, where n is an integer number $\geq 1$ and p corresponds to the axial offset of two neighboring turns of the helix; and
   a reconstruction unit (10) serving for the reconstruction of a CT image, corresponding to the spatial distribution of the absorption within the examination zone (13), from the measuring data acquired by the detector unit (16) within the first measuring window (160), the measuring data derived from rays which extend within a second measuring window being assigned a weight for the reconstruction which differs from that of measuring data derived from rays which extend outside the second measuring window but inside the first measuring window, and the second measuring window being situated, viewed in the direction of the axis of rotation, at the center of the first measuring window and its mutually offset edges (163, 164) being defined by lines which originate from the radiation source (S) and intersect two segments of the helix (17) which are offset over the distance (2m+1)p in the direction of the axis of rotation, where m is an integer number and $0 \leq m < n$.

* * * * *